(12) United States Patent
Parsonage

(10) Patent No.: US 7,863,387 B2
(45) Date of Patent: Jan. 4, 2011

(54) DEHYDROFLUORINATION AND SURFACE MODIFICATION OF FLUOROPOLYMERS FOR DRUG DELIVERY APPLICATIONS

(75) Inventor: Edward Parsonage, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 616 days.

(21) Appl. No.: 11/923,790

(22) Filed: Oct. 25, 2007

(65) Prior Publication Data

US 2009/0111960 A1    Apr. 30, 2009

(51) Int. Cl.
*C08F 114/18*  (2006.01)

(52) U.S. Cl. .................. 525/326.2; 525/326.4; 264/119; 264/120; 264/122; 264/123; 264/126; 264/241; 264/291

(58) Field of Classification Search ............... 525/326.2, 525/326.4; 264/119, 120, 122, 123, 126, 264/241, 291
See application file for complete search history.

(56) References Cited

U.S. PATENT DOCUMENTS

| | | | |
|---|---|---|---|
| 4,678,842 A | 7/1987 | Sandler | |
| 5,041,480 A | 8/1991 | Kawachi et al. | |
| 6,099,562 A | 8/2000 | Ding et al. | |
| 6,923,927 B2 * | 8/2005 | Martakos et al. | ............ 264/119 |
| 2002/0051730 A1 | 5/2002 | Bodnar et al. | |
| 2003/0144727 A1 | 7/2003 | Rosenthal et al. | |
| 2004/0215169 A1 | 10/2004 | Li | |
| 2005/0033417 A1 * | 2/2005 | Borges et al. | .............. 623/1.46 |
| 2005/0113903 A1 | 5/2005 | Rosenthal et al. | |
| 2005/0149163 A1 | 7/2005 | Sahota | |
| 2006/0129727 A1 | 6/2006 | Park | |

FOREIGN PATENT DOCUMENTS

| | | |
|---|---|---|
| FR | 2785812 | 5/2000 |
| WO | 2005046747 | 5/2005 |

OTHER PUBLICATIONS

Bottino, A., Capannelli, U. and Comite, A., "Novel porous membranes from chemically modified poly(vinylidene fluoride)," 273 Journal of Membrane Science, pp. 20-24 (2006).

Wang, S. and Legare, John M., "Perfluoroelastomer and fluoroelastomer seals for semiconductor wafer processing equipment," 122 Journal of Flourine Chemistry, pp. 113-119 (2003).

* cited by examiner

*Primary Examiner*—Bernard Lipman
(74) *Attorney, Agent, or Firm*—Vidas, Arrett & Steinkraus

(57) ABSTRACT

Fluoropolymers having a —CF adjacent to a —CH which are subsequently dehydrofluorinated to create a —C=C— can be used as controlled release carriers for therapeutic agent(s) by covalently conjugating the therapeutic agent(s) to the fluoropolymer at the —C=C—.

23 Claims, 4 Drawing Sheets

DEHYDROFLUORINATION AND SURFACE MODIFICATION OF FLUOROPOLYMERS FOR DRUG DELIVERY APPLICATIONS

FIELD OF THE INVENTION

The present invention relates to the field of controlled, local delivery of pharmacologically active agents, and to polymer compositions useful therein, and to methods of making and using such polymer compositions.

BACKGROUND OF THE INVENTION

Systemic administration of drugs for the treatment of diseases can be effective, but may not be the most efficacious method for diseases which are localized within specific parts of the body. The controlled localized delivery of a drug to diseased tissue has become increasingly desirable because less drug can be administered locally resulting in a corresponding decrease in side effects, as well as providing economic benefit due to the expense of many drugs.

Controlled localized delivery in body lumens can be difficult because the movement of bodily fluids through body lumens such as blood vessels and ducts can carry the drug away from the afflicted area.

Some methods of controlled local delivery of drugs involve inserting or implanting medical devices that include a polymer composition for release of a biologically active material. These polymer compositions may be applied to the surface as a coating. For example, various types of drug-coated stents have been used for localized delivery of drugs to a body lumen. See commonly assigned U.S. Pat. No. 6,099,562 to Ding et al. Such stents have been used to prevent, inter alia, the occurrence of restenosis after balloon angioplasty.

SUMMARY OF THE INVENTION

In one aspect, the present invention relates to a polymer composition for the controlled local delivery of therapeutic agent(s). The polymer composition includes at least one poly (fluoroalkene) containing polymer wherein the sites of unsaturation provide active sites for binding of pharmacologically active agent(s) thereto.

In one aspect, the present invention relates to a polymer composition that may be used as a controlled release carrier for at least one therapeutic agent including at least one fluoropolymer having at least one therapeutic agent is covalently conjugated to the fluoropolymer.

In another aspect, the present invention relates to a method for modifying a fluoropolymer having at least one —CF adjacent to at least one —CH by dehydrofluorination of said at least one —CF and said at least one adjacent —CH to form —C=C—, and covalently conjugating at least one therapeutic agent to said at least one —C=C—.

The polymer compositions may be used in combination with insertable and/or implantable medical devices such as endoprosthetic devices, for example, as a coating disposed thereon.

These and other aspects of the invention are described in the Detailed Description and in the claims below.

DETAILED DESCRIPTION OF THE INVENTION

Figure 1:
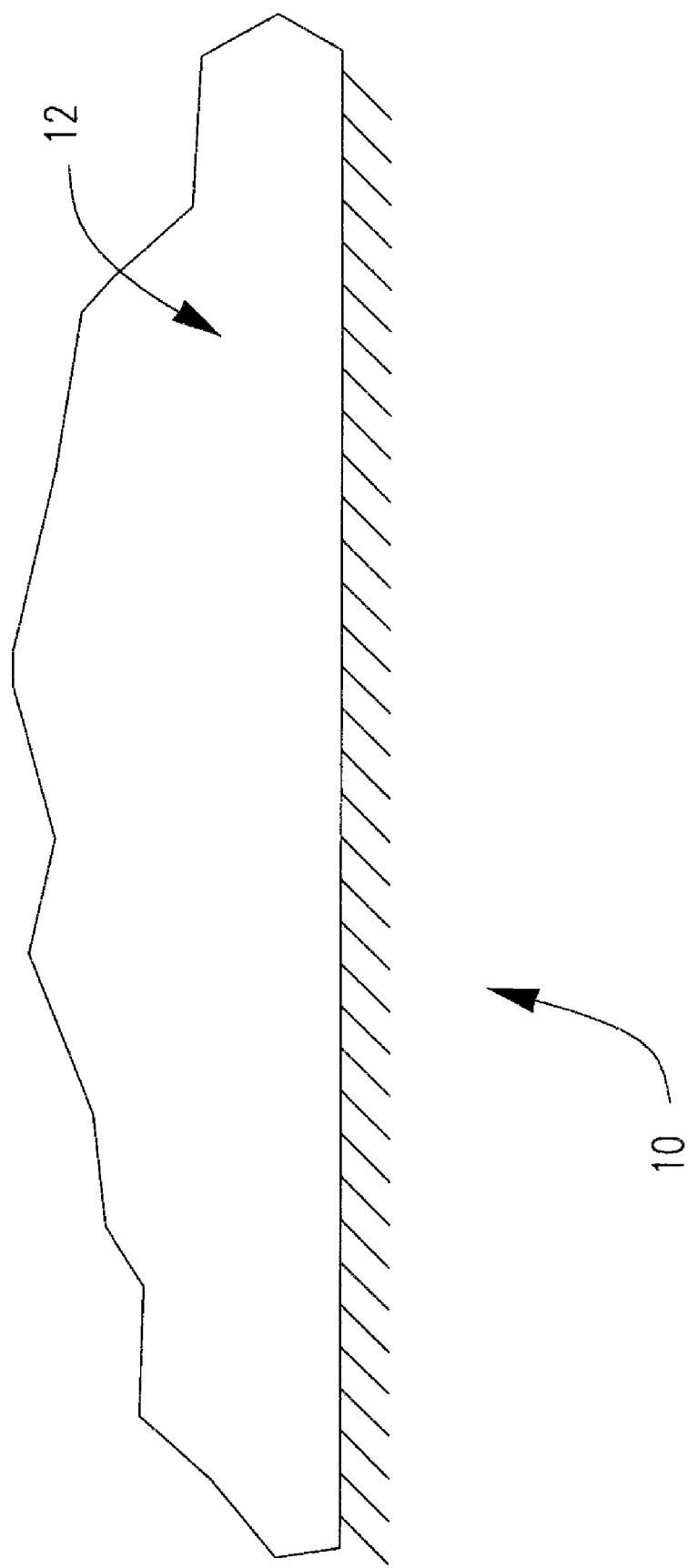
FIG. 1 illustrates a partial surface of a medical device such as an endoprosthetic device with a drug-containing polymer composition according to the invention disposed on the surface.

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The present invention relates to polymer compositions for the controlled local delivery of pharmaceutical agent, and to methods of making the same. The polymer compositions according to the invention include at least one fluoropolymer that has alkenylenic active sites, i.e. —C=C— unsaturation, for binding of pharmacologically active agents. These polymers may be referred to generally as poly(fluoroalkene) containing polymers. As used herein, any fluoropolymer containing unsaturation may be referred to as a poly(fluoroalkene) containing polymer.

The polymers employed in the invention may be fluoropolymers that have been dehydrofluorinated. Suitable polymers for dehydrofluorination have hydrogen and fluorine atoms on adjacent carbon atoms so that extraction of the hydrogen and fluorine results in a C=C double bond. The polymers may include various monomers such as vinylidene fluoride, tetrafluoroethylene, hexafluoropropylene, perfluoromethylvinyl ether and other vinyl ether structures such as cyano-functional vinyl ethers, ethylene and other olefin monomers, chlorotrifluoroethylene and other halogenated monomers, trifluoroethylene and other partially fluorinated monomers and so forth. In some embodiments, the polymer includes at least vinylidene fluoride, hexafluoropropylene, trifluoroethylene or combinations thereof.

Examples of specific polymers include, but are not limited to, homopolymers of vinylidene fluoride or trifluoroethylene, copolymers or terpolymers containing including vinylidene fluoride and at least one copolymer selected from hexafluoropropylene, trifluoroethylene, vinyl fluoride, vinyl chloride, chlorotrifluoroethylene, and mixtures thereof.

Any suitable process of dehydrofluorinating a suitable fluoropolymer as described herein may be employed. For example, exposing a suitable polymer to a basic solution such as onium hydroxide basic solutions, alkoxides, or organic amines to induce dehydrofluorination of the polymer. Examples of specific basic compounds useful herein include, but are not limited to, sodium hydroxide, potassium hydroxide, lithium hydroxide, rubidium hydroxide, quaternary ammonium compounds such as tetrabutylammonium hydroxide and tetrabutylammonium halides, secondary or tertiary alkyl amines, etc., as well as mixtures thereof. Aliphatic, heterocyclic or aromatic amines may be employed, examples of which include, but are not limited to, triethylamine, pyridine, quinoline and salts thereof. Of course, mixtures of any of the basic compounds can also be employed. Dehydrofluorination is described in U.S. Pat. No. 4,678,842, the entire content of which is incorporated by reference herein.

Suitably, dehydrofluorination is accomplished at a solution pH of about 8 to about 14, and more suitably about 10 to about 14.

It may be desirable to also add acid scavengers to minimize reverse hydrohalogenations. Examples of acid scavengers could include, but are not limited to, calcium carbonate or lead stearate.

Surfactants may also be added to the basic composition.

Depending on the basic compound selected for use, the solvent may be either aqueous or organic in nature. Examples of solvents include, but are not limited to, water, N,N-dimethyl formamide, 1-methyl-2-pyrrolidone, triethylphosphate, dimethyl acetamide, dimethyl sulfoxide, methanol, ethanol, butanol, etc. and cosolvent blends.

The above lists are intended for illustrative purposes only, and are not intended as a limitation on the scope of the present invention. Such materials are known to those of ordinary skill in the art.

In one specific embodiment, a copolymer of vinylidene fluoride and hexafluoropropylene is dehydrofluorinated to provide a poly(fluoroalkene) containing polymer. Copolymers vinylidene fluoride and hexafluoropropylene are known to be biostable. The dehydrofluorination process is represented by the following general formula:

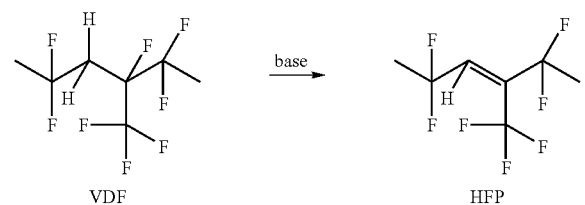

See Bottino, A., Capannelli, U. and Comite, A., Novel porous membranes from chemically modified poly(vinylidene fluoride), 273 Journal of Membrane Science, pp. 20-24 (2006), the entire content of which is incorporated by reference herein. See also Wang, S, and Legare, John M., Perfluoroelastomer and fluoroelastomer seals for semiconductor wafer processing equipment, 122 Journal of Fluorine Chemistry, pp. 113-119 (2003) for other vinylidene fluoride containing polymers which may be employed herein, the entire content of which is incorporated by reference herein.

In some embodiments the dehydrofluorination reaction is conducted to an extent that active sites, i.e. C=C bonds, are produced in the polymer chain in amounts of about 5 mol % or less based on the number of available sites of dehydrohalogenation in the polymer, for instance about 3 mol % or less, in some cases about 1 mol % or less. In some instances the amount is at least about 0.1 mol %.

Dehydrofluorination may be accomplished alone, or concurrently with a further modification of the fluoropolymer described herein, for instance as part of an overall reaction which produces a direct grafting of primary or secondary amines to vinylidene fluoride containing fluoropolymers.

In some cases a nucleophile can be applied directly to displace fluorine atoms of a fluoropolymer to produce a conjugate without isolation of a poly(fluoroalkene) containing polymer.

The site of unsaturation can be employed to modify the fluoropolymer described herein by covalently conjugating a therapeutic agent to the polymer at the unsaturated carbon-carbon double bonds. The modified polymer can then be used for delivery of the therapeutic agent to a desired treatment site within a patient. Of course, two, three or more therapeutic agents may be conjugated to the polymer as well.

Conjugation of the therapeutic agent may be accomplished in some cases by direct bond between the polymer and the therapeutic agent or in other cases by means of an intermediate linking moiety. Suitably the therapeutic agent is bound by a means that allows for gradual release over time, e.g. via hydrolysis or enzymatic reaction at a site of implantation. The rate of release is influenced by several factors, including the type of chemical bond joining the active parent drug to the conjugate moiety.

Many techniques for producing drug conjugates are known. The polymer may be modified using any suitable method known in the art including free radical addition or nucleophilic attack across the double bonds of the poly(fluoroalkene) containing polymer to achieve the desired surface modification. Addition across the double bond may be accomplished directly in some cases where the therapeutic agent has a suitable reactive functionality. In other cases a linking compound may be used that adds to the double bond and also provides a group that will link to the therapeutic agent in a subsequent reaction. For instance a linking compound may provide a carboxy, hydroxy, thiol, or amine group that will link to the therapeutic agent using, e.g. an ester, amide, ether, carbamate, thioester, or thioether bond. In still another example the therapeutic agent is first reacted with a linking compound to produce a derivative that is then reacted with a poly(fluoroalkene) containing polymer to produce a conjugate of the invention.

For example, organic peroxides, polythiols, polyhydroxyl compounds and polyamines are known to add to poly(fluoroalkene) containing polymers in vulcanization reactions. See U.S. Pat. No. 5,041,480, the entire content of which is incorporated by reference herein. These reactions may be modified to provide suitable linkages between a therapeutic agent and a poly(fluoroalkene) in accordance with the present invention.

A nucleophile readily adds across a double bond of a poly (fluoroalkene) containing polymer. Nucleophiles often carry a negative charge, but any compound that is readily attracted to a positive center can be employed as a nucleophile.

Any therapeutic agent that is nucleophilic, or that can be added via a free radical addition to the double bonds of the (fluoroalkene) polymer, or that can be linked via a suitable linking compound as described above, may be employed in the present invention. As used herein, the terms, "therapeutic agent", "drug", "pharmaceutically active agent", "pharmaceutically active material", "beneficial agent", "bioactive agent", and other related terms may be used interchangeably and include genetic therapeutic agents, non-genetic therapeutic agents and cells. A drug may be used singly or in combination with other drugs. Drugs include genetic materials, non-genetic materials, and cells.

Therapeutic agents are disclosed in commonly assigned copending U.S. Patent Publication Nos. 2004/0215169, 2005/0113903 and 2006/0129727, each of which is incorporated by reference herein in its entirety. See also U.S. Patent Publication No. 20050149163, the entire content of which is incorporated by reference herein.

Suitable therapeutic agents that may be added to the double bond include, but are not limited to, cell adherent compounds, endothelial cells, functional groups, growth enhancing factors, etc.

More specifically, compounds having amine groups, amino acids, carbohydrates, sugars, alcohols, chelating and/or ligand groups, enzymes, catalysts, hormones, lectins, proteins, peptides, antibiotics, vitamins, antigens, nucleic acids, DNA, RNA, etc., may be added to the fluoropolymers described herein.

If a linking compound is used it may be for instance an oligopeptide, a polyether, a polyester, a functionalized silane, etc.

Some exemplary therapeutic agents include, but are not limited to, anti-inflammatory agents such as dexamethasone, prednisolone, corticosterone, budesonide, estrogen, sulfasalazine, mesalamine, and analogues thereof; antineoplastic/antiproliferative/anti-miotic agents such as paclitaxel, everolimus, 5-fluorouracil, cisplatin, vinblastine, vincristine, rapamycin, epothilones, endostatin, angiostatin, thymidine kinase inhibitors, and analogues thereof, anesthetic agents such as lidocaine, bupivacaine, ropivacaine, and analogues thereof, anti-coagulants; integrins, chemokines, cytokines and growth factors.

Some preferred therapeutic agents for use herein include, but are not limited to, anti-restenosis drugs, such as paclitaxel, sirolimus, everolimus, tacrolimus, dexamethoasone, estradiol, ABT-578 (Abbott Laboratories), trapidil, liprostin, Actinomycin D, Resten-NG, Ap-17, clopidogrel and Ridogrel.

The polymer compositions according to the invention can be employed as drug delivery coatings on any of a variety of insertable and/or implantable medical devices. Examples include, but are not limited to stents including both self-expanding and balloon-expandable stents, stent-grafts, dilatation balloons, any type of catheter assembly and any component thereof including, but not limited to, central venus catheters, diagnostic catheters and cardiovascular catheters, extracorpeal circuits, vascular grafts, pumps, heart valves, and cardiovascular sutures, blood exchanging devices, vascular access ports, to name a few. Regardless of detailed embodiments, applicability of the invention should not be considered limited with respect to implant design, implant location or materials of construction. Further, the present invention may be used with other types of implantable prostheses not specifically mentioned herein.

In some embodiments a device such a medical device is provided with a coating layer of a suitable fluoropolymer so that the layer has a device interface on one side and an exterior surface on the other side and then the exterior surface of the coating layer is subjected to the reactions of dehydrofluorination and conjugation with therapeutic agent. In some such embodiments, for instance in coated endoprosthetic devices such as stents, the reactions may be controlled so that the integrity and/or composition of the coating at the device interface is substantially unaltered so that as the therapeutic agent is released continuity of the polymer coating is maintained.

In other embodiments the polymer/therapeutic agent conjugates may be formed first and then applied to a suitable medical device substrate. In still other embodiments an implantable medical device may be formed of a polymer/therapeutic agent conjugate of the invention.

Turning now the figures, FIGS. 1-4 illustrate drug delivery polymer coatings on some exemplary embodiments of a medical device. These embodiments are intended for illustrate purposes only, and not as a limitation on the scope of the present invention.

FIG. 1 illustrates a partial surface of a medical device 10 such as an endoprosthetic device with a drug-containing polymer composition 12 according to the invention disposed on the surface.

Figure 2:
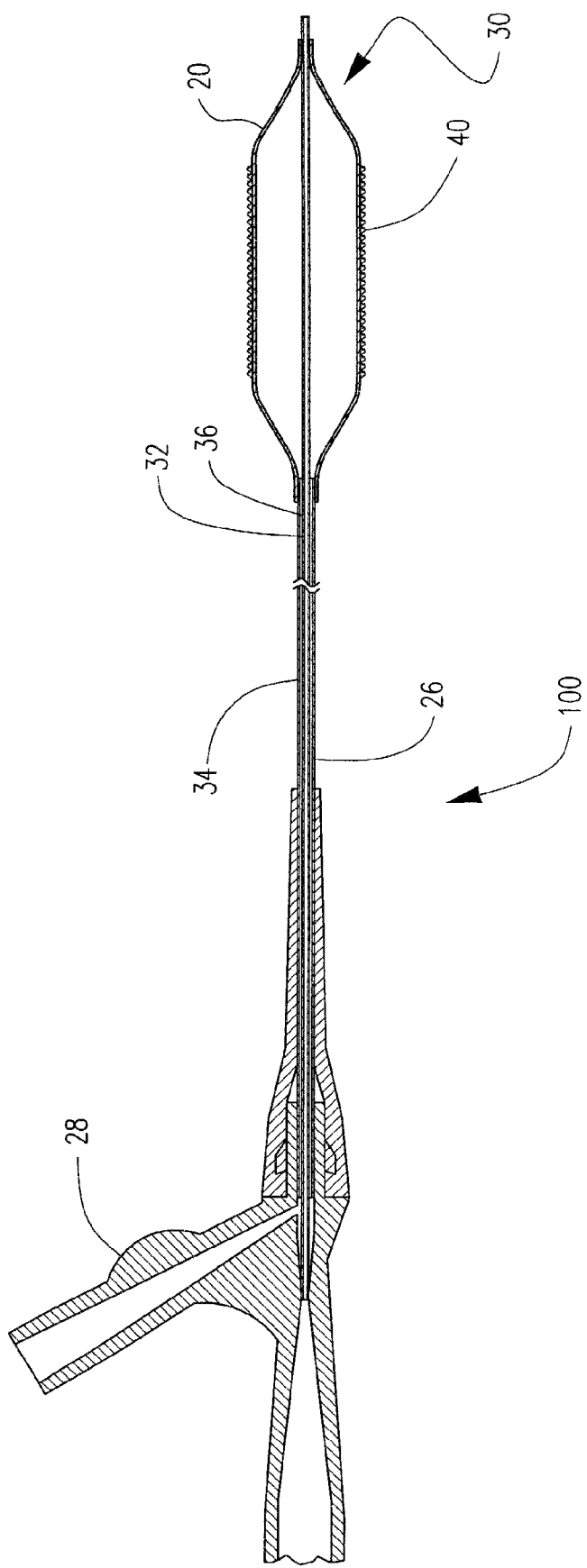
FIG. 2 is longitudinal cross-sectional view of a catheter assembly in accordance with which the drug-containing polymer compositions according to the invention may be employed.

FIG. 2 is longitudinal cross-sectional view of a catheter assembly 100 in accordance with which the drug-containing polymer compositions according to the invention may be employed. In this embodiment, catheter assembly 100, is employed for purposes of delivering an endoprosthetic device, in this embodiment, a balloon-expandable stent 40, is disposed on an expandable balloon member 20. Balloon member 20 in combination with stent 40 is disposed about the distal end of the catheter assembly, in this embodiment, a dual lumen catheter assembly having an inner shaft 32, an outer shaft 34, and an inflation lumen 36 through which inflation fluid can be transported to the interior of balloon 20.

Figure 3:
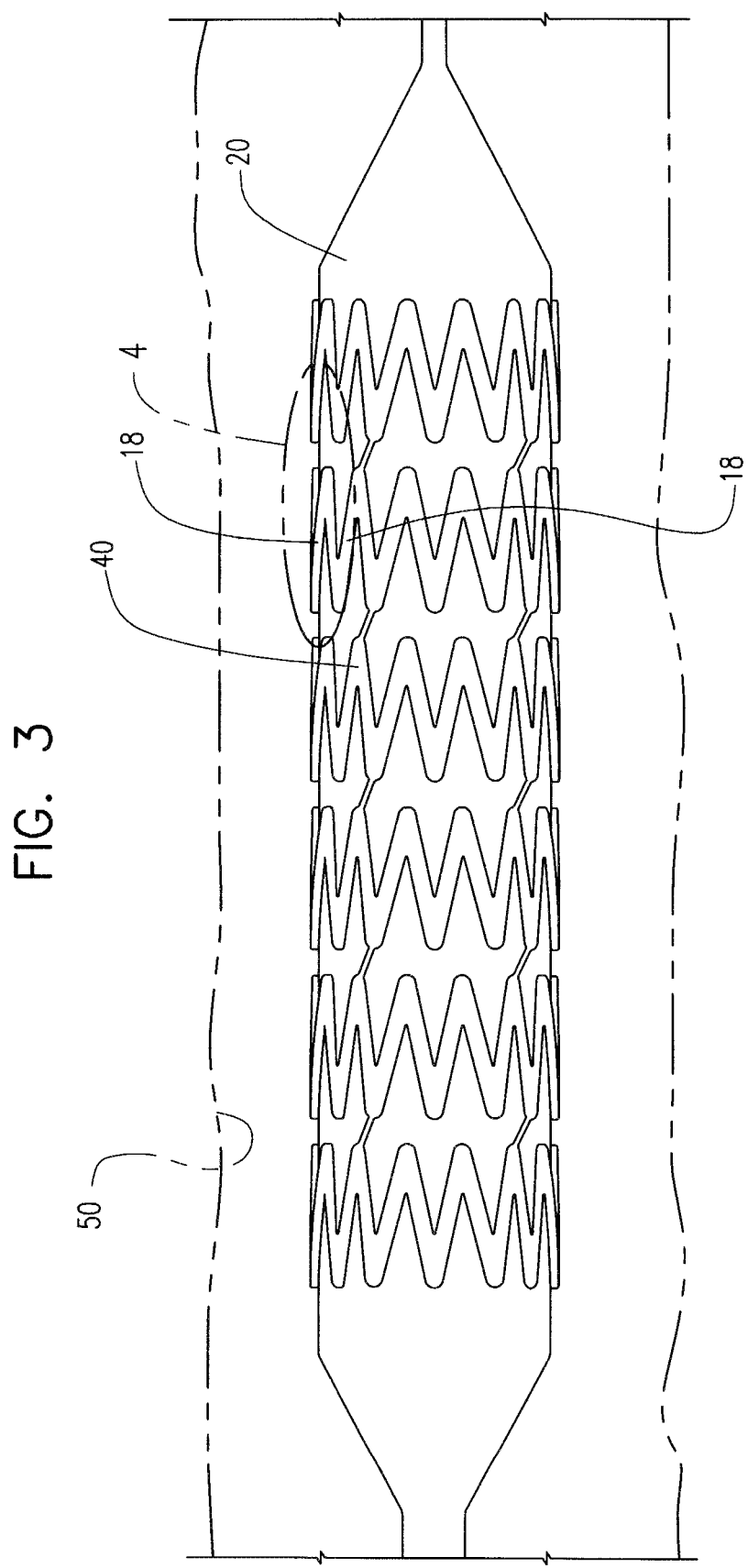
FIG. 3 is longitudinal side view of a stent disposed on a medical balloon, the stent having a drug-containing polymer composition according to the invention disposed thereon.
Figure 4:
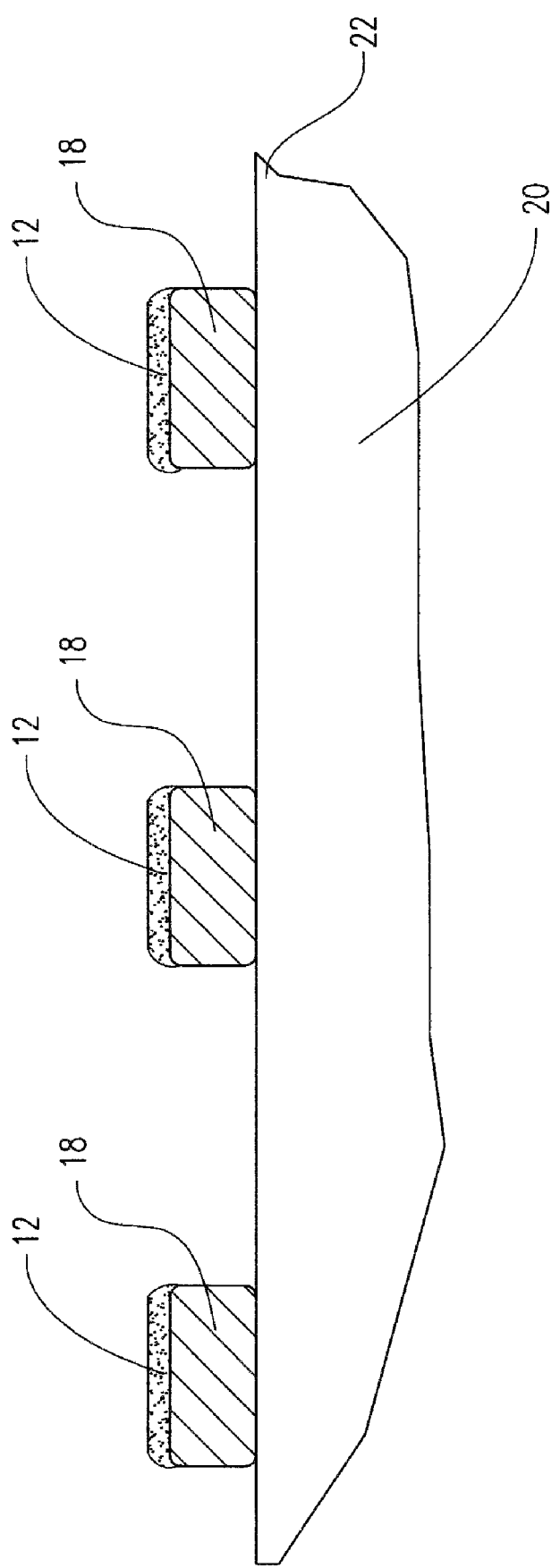
FIG. 4 is a fragmentary cross-section of a stent and balloon taken along the longitudinal axis of the balloon and having a drug-containing polymer composition disposed on the stent.

The drug delivery polymer compositions according to the invention can be disposed on any of the components of the catheter assembly. In one embodiment, drug delivery polymer composition 12 is disposed on stent 40 as illustrated in FIGS. 3 and 4. FIG. 3 is an expanded longitudinal side view of a stent 40 similar to that shown in FIG. 2, disposed on a expandable balloon member 20, stent 40 having a drug-containing polymer composition 12 according to the invention disposed thereon.

FIG. 4 is a fragmentary cross-section stent 40 and expandable balloon member 20 taken at section 4 in FIG. 3. Drug delivery polymer composition 12 is shown disposed on stent struts 18 in FIG. 4. While the coating 12 is shown on only one surface 17 (i.e. outer stent surface) of the struts 18, it should be noted that depending on the application method employed, the coating could be on the sides 19 of struts 18, as well as on the bottom 21 (i.e. inner surface) of the stent struts 18 as well. For example, while spraying may produce a coating on the outer surface 17 and the sides 19 of struts 18, dipping of stent 40 may produce a coating on all surfaces (17, 19 and 21), and brushing may produce a coating on only the outer surface 17 of struts 18.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A polymer composition comprising a fluoropolymer having at least one therapeutic agent conjugated therewith by a covalent linkage between said polymer and said therapeutic agent, said polymer composition is a product produced by providing a fluoropolymer having active sites of —C═C— unsaturation and binding at least one therapeutic agent directly thereto at one or more of said active sites or through a linking group that binds to the polymer at said active sites.

2. A polymer composition as in claim 1 wherein the fluoropolymer having active sites of —C═C— unsaturation is provided by dehydrofluorination of a fluoropolymer having at least one carbon atom that is bound to a hydrogen atom and also to a second carbon atom, the second carbon being bound to a fluorine atom.

3. A polymer composition as in claim 2 wherein said fluoropolymer prior to dehydrofluorination comprises repeating units of vinylidene fluoride, trifluoroethylene tetrafluoroethylene, hexafluoropropylene, perfluoromethylvinyl ether, chlorotrifluoroethylene, trifluoroethylene or mixtures thereof.

4. The polymer composition of claim 2 wherein said fluoropolymer prior to dehydrofluorination composition comprises vinylidene fluoride and hexafluoropropylene.

5. The polymer composition of claim 2 wherein said fluoropolymer, after dehydrofluorination and prior to conjugation of said at least one therapeutic agent, comprises about 0.1 mol % to about 5 mol —C═C— unsaturation.

6. The polymer composition of claim 2 wherein said fluoropolymer, after dehydrofluorination and prior to conjugation of said at least one therapeutic agent, comprises about 0.1 mol % to about 1 mol % of C═C unsaturation.

7. The polymer composition of claim 1 wherein the therapeutic agent is releasable by hydrolysis or by enzymatic reaction.

8. The polymer composition of claim 1 wherein said fluoropolymer has at least two therapeutic agents conjugated therewith.

9. An endoprosthetic device having a polymer composition as in claim 1 disposed on at least a portion of a surface thereof.

10. The device of claim 9 wherein said endoprosthetic device is a stent.

11. The stent of claim 10 mounted on a catheter assembly.

12. A method of covalently conjugating at least one therapeutic agent to a polymer for the controlled release of said at least one therapeutic agent at a treatment site within a patient, the method comprising:
providing at least one fluoropolymer comprising at least one —CF adjacent to at least one —CH;
dehydrofluorinating said fluoropolymer wherein said at least one —CF adjacent at least one —CH form at least one —C═C—; and
covalently conjugating at least one therapeutic agent to at least one —C═C—.

13. The method of claim 12 wherein the at least one therapeutic agent is covalently conjugated by a direct bond or an intermediate linking group and wherein the therapeutic agent is releasable by hydrolysis or by enzymatic reaction.

14. The method of claim 12 wherein said dehydrofluorination of said fluoropolymer is accomplished by the addition of at least one basic compound.

15. The method of claim 14 wherein said defluorinating is accomplished at a pH of about 10 to about 14.

16. The method of claim 14 wherein said at least one basic compound is selected from the group consisting of onium hydroxides, alkoxides, organic amines and mixtures thereof.

17. The method of claim 12 wherein said at least one therapeutic agent is covalently conjugated to at least one —C═C— by a mechanism selected from the group consisting of free radical addition and nucleophilic attack at said —C═C—.

18. The method of claim 12 wherein said fluoropolymer comprising about 0.1 mol % to about 5 mol % of said at least one —C═C— after dehydrofluorination.

19. The method of claim 12 wherein said fluoropolymer comprises repeat units of at least one member selected from the group consisting of vinylidene fluoride, trifluoroethylene and mixtures thereof prior to dehydrofluorination.

20. The method of claim 12 wherein said fluoropolymer comprises repeat units of vinylidene fluoride, and at least one member selected from the group consisting of tetrafluoroethylene, hexafluoropropylene, perfluoromethylvinyl ether, chlorotrifluoroethylene, trifluoroethylene and mixtures thereof prior to dehydrofluorination.

21. The method of claim 12 wherein said fluoropolymer comprises repeat units of vinylidene fluoride and hexafluoropropylene prior to defluorination.

22. A medical device comprising a polymer composition disposed on at least a portion of a surface of said medical device, said polymer composition comprising at least one fluoropolymer having active sites of —C═C— unsaturation and at least one therapeutic agent conjugated to said at least one fluoropolymers through active sites of —C═C— unsaturation.

23. An expandable medical balloon having a polymer composition as in claim 1 disposed on at least a portion of a surface thereof.

* * * * *